(12) United States Patent
Lo

(10) Patent No.: US 8,308,662 B2
(45) Date of Patent: Nov. 13, 2012

(54) MEASURING DEVICE

(75) Inventor: Ian Lo, Calgary (CA)

(73) Assignee: Arthrex, Inc., Naples, FL (US)

( * ) Notice: Subject to any disclaimer, the term of this patent is extended or adjusted under 35 U.S.C. 154(b) by 796 days.

(21) Appl. No.: 11/952,169

(22) Filed: Dec. 7, 2007

(65) Prior Publication Data

US 2008/0306408 A1    Dec. 11, 2008

Related U.S. Application Data

(60) Provisional application No. 60/868,947, filed on Dec. 7, 2006.

(51) Int. Cl.
*A61B 5/103* (2006.01)
*A61B 5/117* (2006.01)
*A61B 5/04* (2006.01)

(52) U.S. Cl. .................. 600/587; 600/511; 600/512

(58) Field of Classification Search .......... 600/587; 33/511, 512, 832; 606/79, 102
See application file for complete search history.

(56) References Cited

U.S. PATENT DOCUMENTS

| | | | |
|---|---|---|---|
| 2,763,935 A * | 9/1956 | Whaley et al. ............... 33/511 |
| 3,478,435 A | 11/1969 | Cook | |
| 4,450,834 A | 5/1984 | Fischer | |
| 4,645,491 A | 2/1987 | Evans | |
| 4,779,349 A | 10/1988 | Odensten et al. | |
| 4,863,423 A | 9/1989 | Wallace | |
| 5,010,892 A | 4/1991 | Colvin et al. | |
| 5,013,318 A | 5/1991 | Spranza | |
| 5,171,248 A | 12/1992 | Ellis | |
| 5,180,388 A | 1/1993 | DiCarlo | |
| 5,292,309 A | 3/1994 | Van Tassel et al. | |
| 5,312,351 A | 5/1994 | Gerrone | |
| 5,320,608 A | 6/1994 | Gerrone | |
| 5,403,264 A | 4/1995 | Wohlers et al. | |
| 5,860,923 A * | 1/1999 | Lenker et al. ............... 600/433 |
| 5,895,389 A | 4/1999 | Schenk et al. | |
| 6,039,753 A | 3/2000 | Meislin | |
| 6,159,167 A * | 12/2000 | Hardin-Naser ............... 600/587 |
| 6,159,179 A | 12/2000 | Simonson | |
| 6,224,608 B1 | 5/2001 | Ciccolella et al. | |
| 6,427,351 B1 | 8/2002 | Matthews et al. | |
| 6,729,037 B2 | 5/2004 | White | |
| 6,764,453 B2 * | 7/2004 | Meier ............... 600/587 |
| 6,893,421 B1 | 5/2005 | Larson et al. | |
| 7,134,216 B2 | 11/2006 | Rupp et al. | |
| 7,166,112 B2 * | 1/2007 | Hawkins et al. ............... 606/102 |
| 2002/0104230 A1 | 8/2002 | White | |
| 2004/0068190 A1 | 4/2004 | Cespedes | |

(Continued)

FOREIGN PATENT DOCUMENTS

JP    2006081624    3/2006

(Continued)

*Primary Examiner* — Rene Towa
*Assistant Examiner* — Adam Eiseman
(74) *Attorney, Agent, or Firm* — Cohen & Grigsby, P.C.

(57) ABSTRACT

A measuring device for measuring a depth of a tear of a tissue is disclosed. The measuring device comprises a member having a shaft and a distal tip, a plurality of indicia on the shaft of the member for measuring the depth of the tear, and a cannulated member into which the member is disposed. In an example, the measuring device is used to measure the depth of a tear of the rotator cuff tendon. A method of measuring a tear of a tissue using the measuring device is also disclosed.

13 Claims, 6 Drawing Sheets

U.S. PATENT DOCUMENTS

| | | |
|---|---|---|
| 2004/0193175 A1* | 9/2004 | Maroney et al. .............. 606/102 |
| 2004/0267164 A1 | 12/2004 | Rhodes et al. |
| 2005/0004513 A1 | 1/2005 | Beyerlein |
| 2005/0027215 A1 | 2/2005 | Baxter-Jones et al. |
| 2005/0066535 A1 | 3/2005 | Rupp et al. |
| 2005/0137600 A1* | 6/2005 | Jacobs et al. .................... 606/79 |
| 2005/0187519 A1 | 8/2005 | Harris et al. |
| 2006/0207118 A1 | 9/2006 | Kim |
| 2006/0207119 A1 | 9/2006 | Kim et al. |
| 2006/0224161 A1 | 10/2006 | Bhattacharyya |

FOREIGN PATENT DOCUMENTS

| | | |
|---|---|---|
| WO | 0247549 | 6/2002 |
| WO | WO 2005027745 | 3/2005 |

* cited by examiner

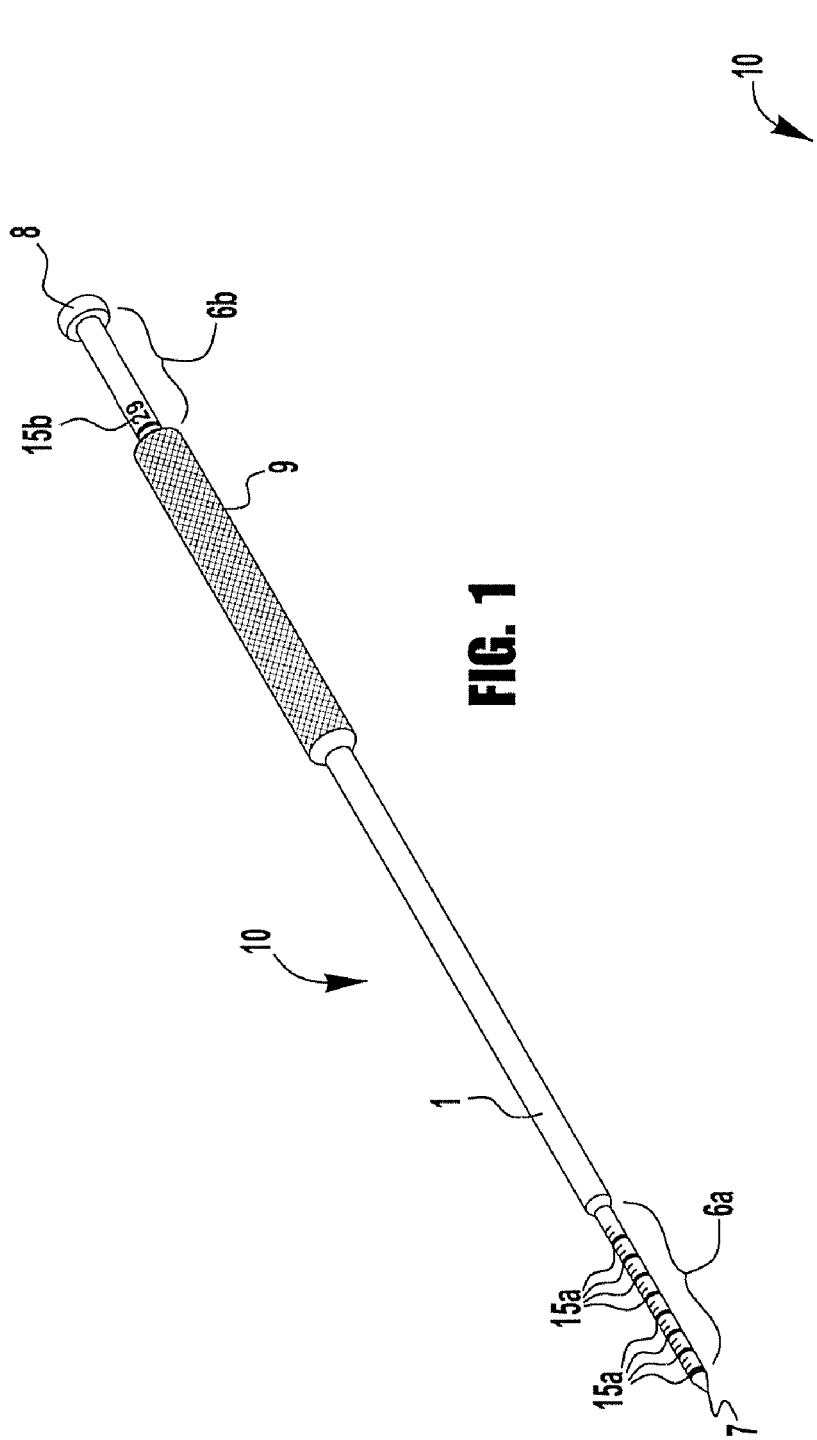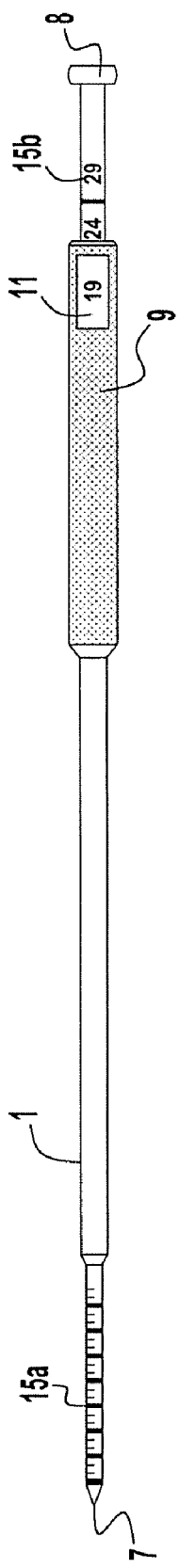

MEASURING DEVICE

RELATED APPLICATION

This application is a non-provisional filing of and claims priority to U.S. Provisional Patent Application No. 60/868,947, filed Dec. 7, 2006 incorporated herewith in its entirety.

BACKGROUND

Rotator cuff tears are a common source of shoulder pain and result from tendon degeneration or sports-related injury or other trauma. Partial thickness defects of the rotator cuff result when the tendon is incompletely detached from the humeral head. One method of treatment for rotator cuff tears is a surgical procedure to reattach the tendon to the humeral head from where it is torn. In the case of partial tears, treatment options include non-surgical procedures such as physical therapy and/or a surgical procedure in which the tendon is completely detached from the humeral head, followed by reattachment of the tendon thereto. The size or depth of the tear is an important factor that is considered when determining the appropriate treatment for a partial tear of the rotator cuff, with surgery being the generally preferred treatment when more than 50 percent of the tendon is torn from the humeral head and non-surgical options being generally preferred when less than 50 percent of the tendon is torn from the humeral head.

SUMMARY

In an embodiment, a measuring device for measuring a depth of a tear of a tissue is disclosed. The measuring device comprises: a member having a shaft and a distal tip, there being a plurality of indicia on the shaft of the member for measuring the tissue tear; and a cannulated member into which the member is disposed. In an example, the member is solid. In another example, the plurality of indicia comprises a first plurality of indicia disposed on a distal portion of the shaft and a second plurality of indicia disposed on a proximal portion of the shaft. In an example, the tissue is a rotator cuff tendon.

In another embodiment, a method of measuring a tear of a tissue using the measuring device is disclosed. The method of measuring comprises the steps of: sliding the member within the cannulated member so that the distal tip of the member is substantially positioned at a distal margin, wherein the measuring device is positioned substantially tangential to the tear; moving the cannulated member so that a distal end of the cannulated member is substantially at a proximal margin while substantially maintaining the position of the distal tip of the member at the distal margin; and reading the indicia. In an example, the first plurality of indicia is read to measure a depth of the tear of the tissue and the second plurality of indicia is read to measure a thickness of the tissue. In an example, the depth of the tear of the tissue and the thickness of the tissue are used to calculate the percentage of the tissue that is torn and to decide whether to surgically repair the tear.

Other advantages of the present invention will become apparent from a perusal of the following detailed description of presently preferred embodiments taken together with the accompanying drawings.

BRIEF DESCRIPTION OF THE FIGURES

FIG. 1 is a perspective view according to an embodiment of the measuring device.

FIG. 3 is a side view according to an embodiment of the measuring device.

DETAILED DESCRIPTION

Figure 2:
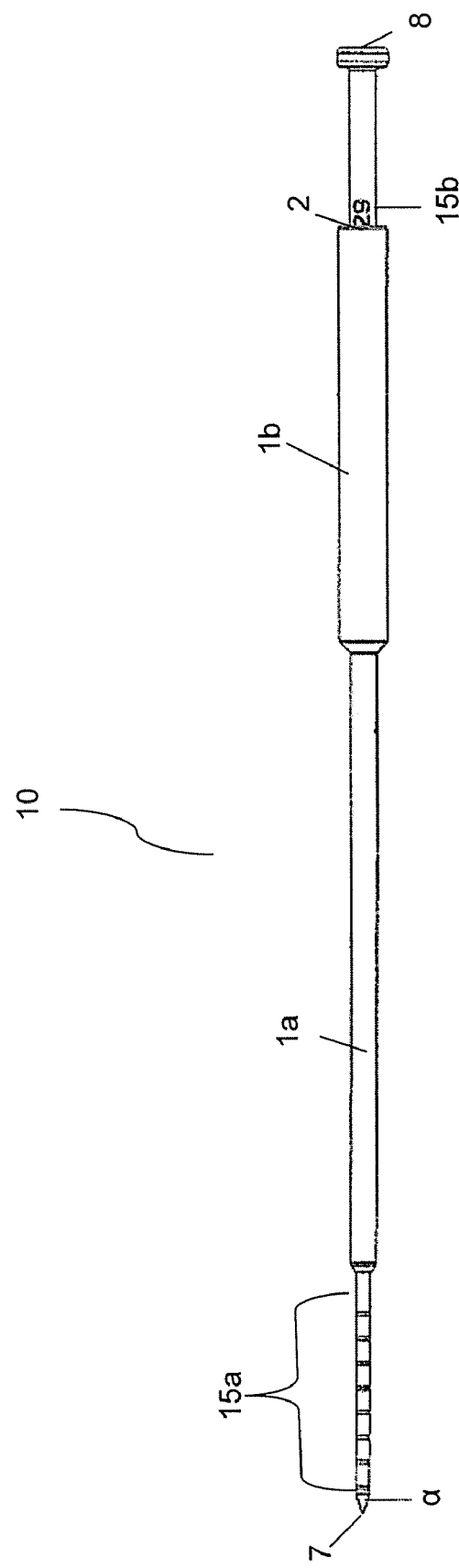
FIG. 2 is a side view according to an embodiment of the measuring device.

Referring initially to FIGS. 1-3, an embodiment of the measuring device 10 is shown. The measuring device 10 measures the depth t of a tear of a tissue 150 from its point of attachment 152, shown in FIG. 6 as a rotator cuff. In an embodiment, the measuring device 10 also measures the thickness T of the tissue 150. See, e.g., FIG. 6C. The measuring device 10 is optionally used arthroscopically which can provide access and magnification. As shown in the figures, measuring device 10 comprises a member 5 and a cannulated member 1 into which the member 5 is disposed. In an example, member 5 slides within cannulated member 1. In an example, member 5 is solid. In examples, the measuring device 10 is made of stainless steel, titanium, or other metals, or Polyaryletheretherketone (PEEK) or other hard plastics. The measuring device 10 is of a length and diameter appropriate for ease of handling and sufficient to extend the depth t of a tear and thickness T of the tissue 50.

Figure 4:
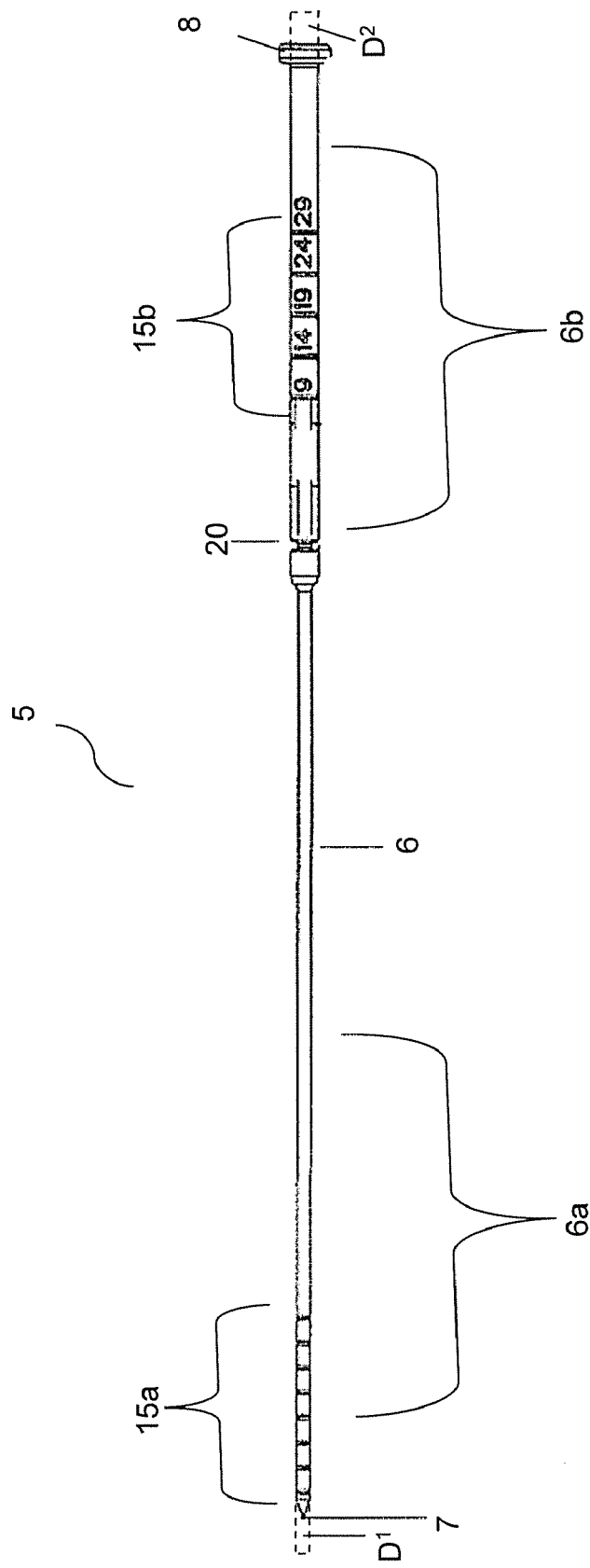
FIG. 4 is a detail view of the solid member according to an embodiment of the measuring device.

As shown in detail in FIG. 4, member 5 has a shaft 6 and a distal tip 7 configured to penetrate through a tear in a tissue (not shown). In an example, the distal tip 7 is beveled to facilitate penetration of the tissue 50, including ligament, muscle, tendon or the like. Shaft 6 has distal and proximal portions 6a, 6b. In an example, the distal portion 6a of the shaft 6 has an outer diameter $D^1$ that is less than an outer diameter $D^2$ of the proximal portion 6b of the shaft 6. As shown generally in the figures, in an example, measuring device 10 further comprises a head 8 disposed on the member 5 at an end of the shaft 6 opposite the distal tip 7. Head 8 has a diameter that is greater than the outer diameter of the proximal portion 1b of cannulated member 1. Optionally, and as shown in FIG. 4, the shaft 6 of the member 5 is configured with an indentation to receive a seal 20 such as an O-ring that stabilizes the member 5 within the cannulated member 1 or to seal member 5 from cannulated member 1.

In examples, the distal portion 6a of the shaft 6 has an outer diameter $D^1$ of about 0.05 inches to about 0.08 inches, and preferably about 0.06 inches, and the proximal portion 6b of the shaft 6 has an outer diameter $D^2$ of about 0.101 inches to about 0.169 inches, and preferably about 0.135 inches. In an example such as illustrated in FIG. 2, distal tip 7 has an angle α of about 30° to about 50°, and preferably of about 40°.

As shown generally in the figures, there is a plurality of indicia 15 on the shaft 6 of member 5 for measuring the depth t of a tear of a tissue 50 or the distance from the bone from which the tissue has torn, such as measuring the depth t in millimeters. In the example shown in FIG. 4, the plurality of indicia 15 comprises a first plurality of indicia 15a disposed on the distal portion 6a of the shaft 6 and a second plurality of indicia 15b disposed on the proximal portion 6b of the shaft 6. First plurality of indicia 15a measures the depth t of the tear of the tissue 50 and second plurality of indicia 15b measures a total thickness T of the tissue 50. The function of the plurality of indicia 15 is explained in more detail below. In use, head 8 contacts proximal end 2 of cannulated member 1 when member 5 is maximally extended.

Figure 5:
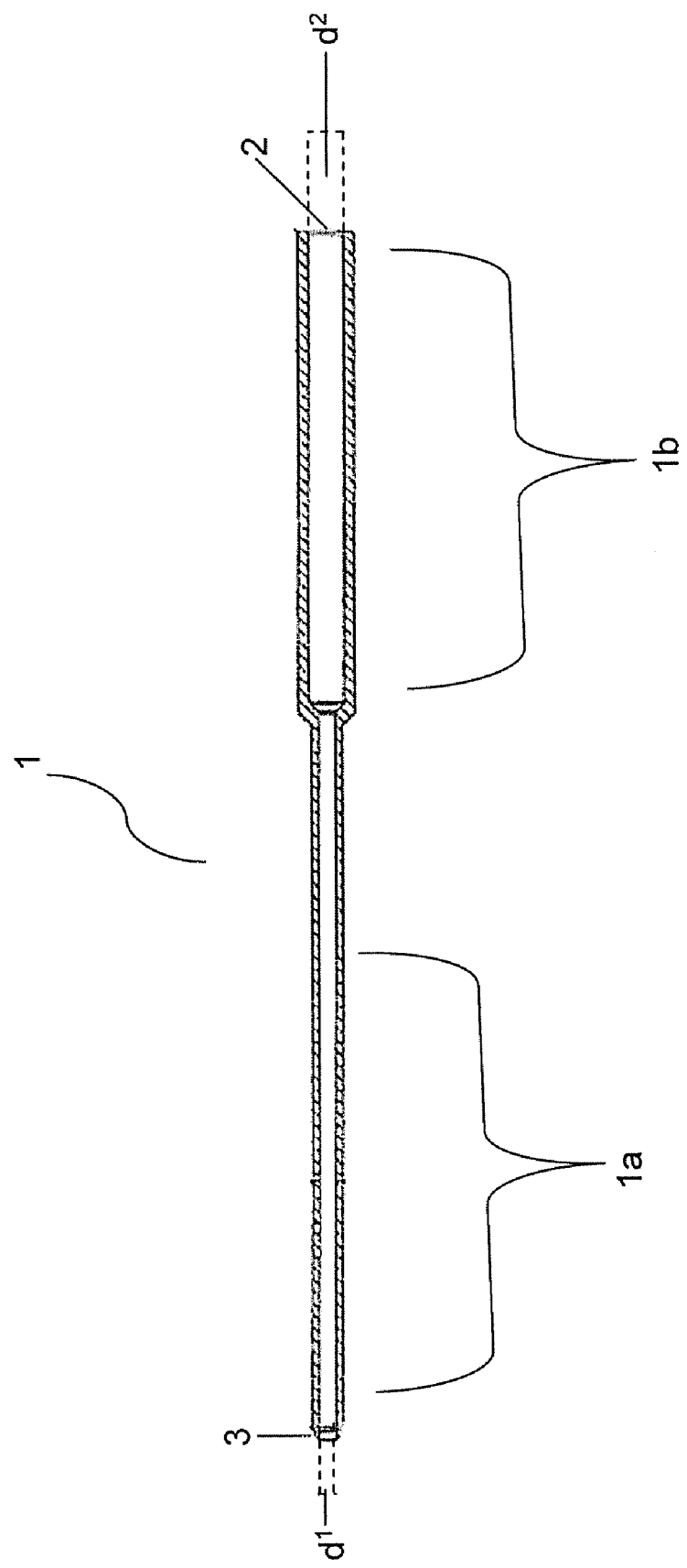
FIG. 5 is a cross-sectional detail view of the cannulated member according to an embodiment of the measuring device.

As shown in detail in FIG. 5, cannulated member 1 has a distal portion 1a and a proximal portion 1b. In an example, the distal portion 1a of the cannulated member 1 has an outer diameter $d^1$ that is less than an outer diameter $d^2$ of the proximal portion 1b of the cannulated member 1. In an example, cannulated member 1 optionally further comprises a grip 9, as shown in the examples in FIGS. 1 and 3. In another example, cannulated member 1 further comprises a window 11 positioned to view at least a portion of the plurality of indicia 15 disposed on the shaft 6. FIG. 3 shows the window 11 positioned to view a portion of the plurality of indicia 15b disposed on the proximal portion 6b of the shaft 6. In an example, the cannulated member 1 comprises a trocar (not shown) to facilitate introduction of the device 10 into the tissue.

In examples, the distal portion 1a of the cannulated member 1 has an inner diameter $d^1$ of about 0.053 inches to about 0.089 inches, and preferably about 0.071 inches, and the proximal portion 1b of the cannulated member 1 has an inner diameter $d^2$ of about 0.113 inches to about 0.188 inches, and preferably about 0.150 inches.

In another embodiment, a method of performing orthopedic surgery is disclosed, the method comprising the steps of using the measuring device 10 to measure the depth t of a tissue tear, such as tears of a ligament, tendon, muscle, or the like, including the distance from the point of attachment 152 (shown in FIG. 6 as the humeral head) from which the tissue 150 (shown as the rotator cuff) has torn. In examples, the measuring device 10 may be used in surgeries to repair tears of the rotator cuff 150, such as partial articular surface tendon avulsion (PASTA) tears. In examples, the measurement device 10 is positioned substantially tangential to the tear by way of arthroscopic or open surgical means. Optionally, the measurement device 10 is positioned by penetrating the distal tip 7 through the tear, such as by using a stab incision.

Figure 6A:
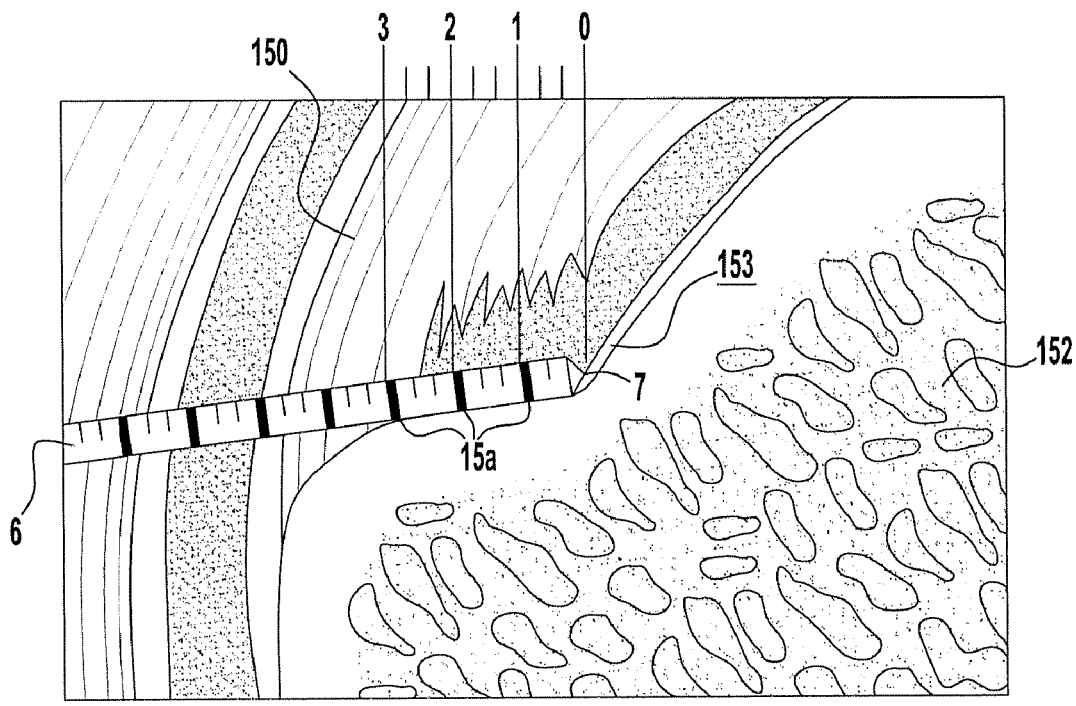
FIG. 6 is a schematic that shows an embodiment of the measuring device in use where the tissue is a rotator cuff.
Figure 6B:
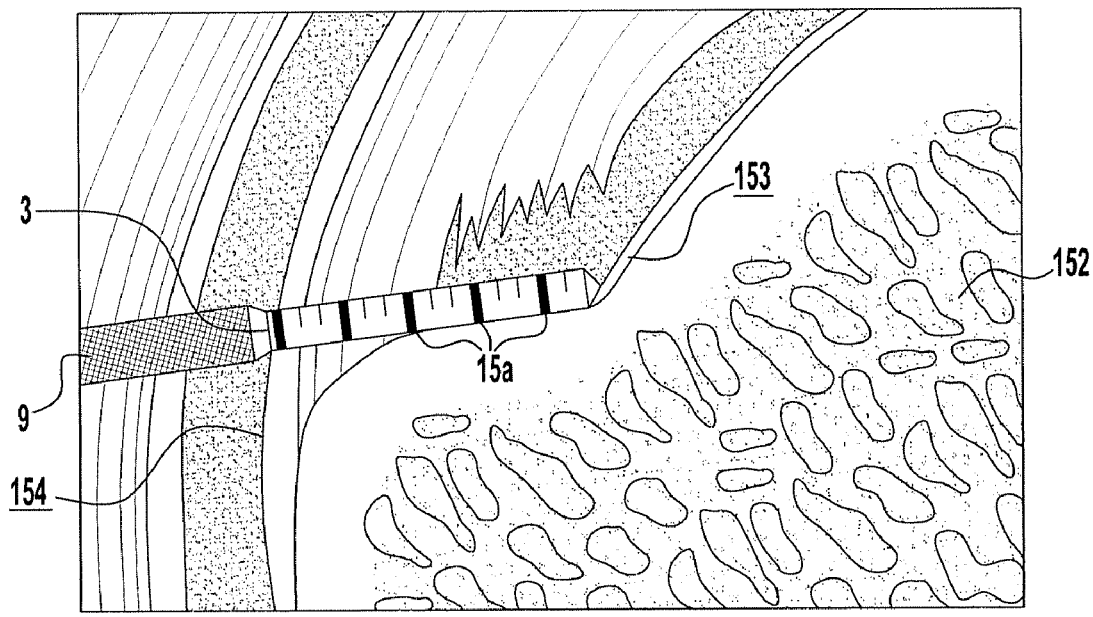
Figure 6C:
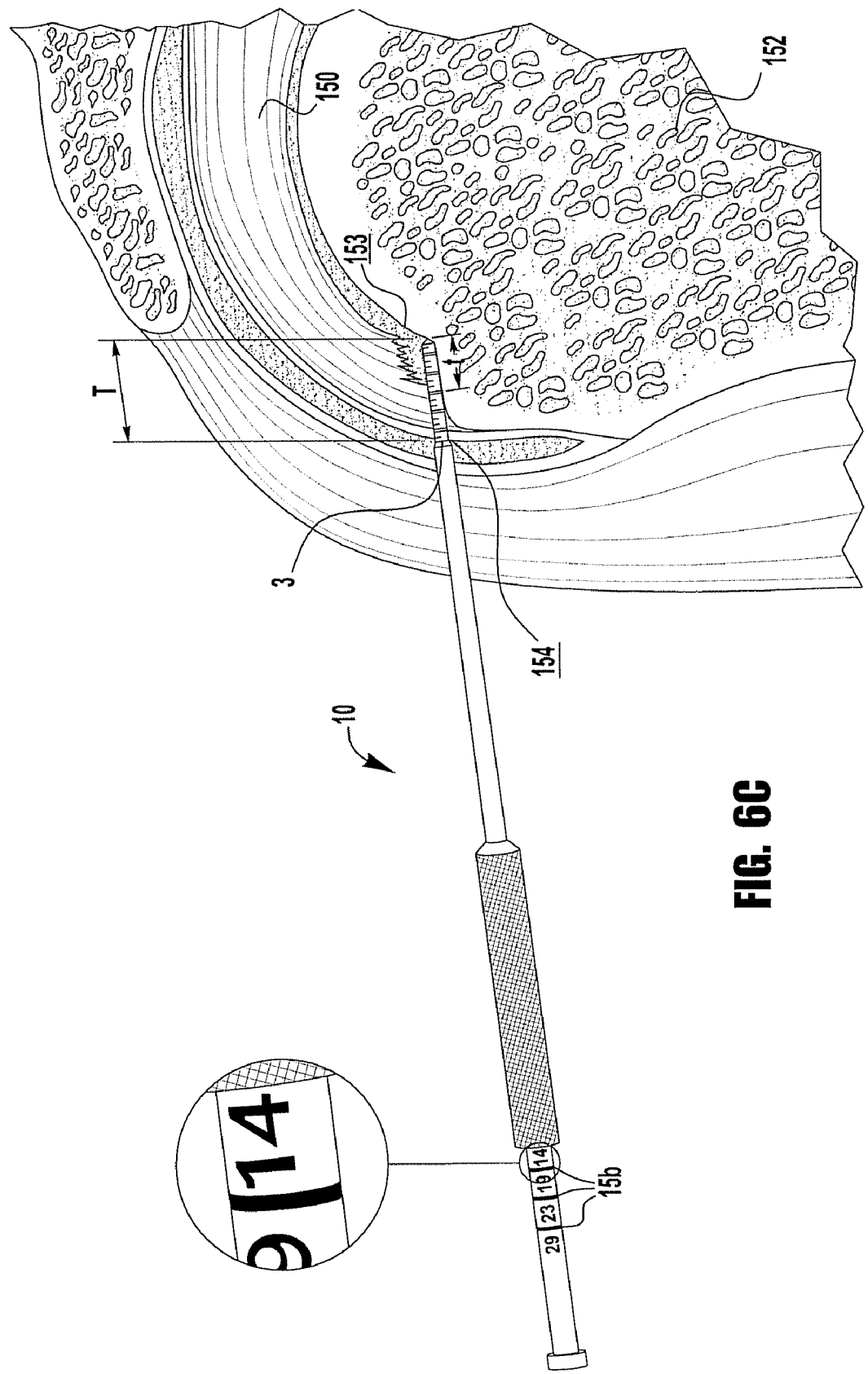

In a first step of measuring a tear of a tissue 150 using the measuring device 10, member 5 is slid within the cannulated member 1 so that the distal tip 7 of member 5 is substantially positioned at a distal margin 153 (shown in FIG. 6 as the articular margin). In this position, at least a portion of a plurality of indicia 15 is exposed on the shaft 6 of member 5, such as the first plurality of indicia 15a exposed on the distal portion 6a of the shaft depicted in FIGS. 6A, 6C. In an example, the step of sliding the member 5 within the cannulated member 1 to position the distal tip 7 at the distal margin 153 is performed while viewing the tissue intraarticularly.

In a next step, cannulated member 1 is moved so that the distal end 1a of the cannulated member 1 is substantially positioned at a proximal margin 154 (shown in FIG. 6 as the bursal side) while substantially maintaining the position of the distal tip 7 of member 5 at the distal margin 53 (see FIG. 6B). In this position, at least a portion of a plurality of indicia 15 is exposed on the shaft 6 of member 5, such as the second plurality of indicia 15b exposed on the proximal portion 6b of the shaft depicted in FIG. 6C. In an example, the step of moving the cannulated member 1 to the proximal margin 154 is performed while viewing the tissue from a subacromial viewing position.

In a next step, the plurality of indicia 15 are read. The depth t of the tear in the tissue 150 is measured using the first plurality of indicia 15a and is equal to the size of the distal portion 6a of the shaft 6 that is exposed between the distal tip 7 positioned at the distal margin 153 and the distal edge of the tissue tear, as shown in FIG. 6. In an example, the depth t is measured by counting the number of indicia exposed. In the example shown in FIG. 6A, the depth of the tear t of the rotator cuff tendon 150 is equal to the size of the distal portion 6a of shaft 6 that is exposed between distal tip 7 positioned at articular margin 153 and the distal edge of the tear 155. In FIG. 6A, three indicia are exposed, the indicia appearing in 3 mm increments, so the depth t of the tear is 9 mm. In other examples, the indicia are positioned at other increments.

The total thickness of the tissue T is measured using the second plurality of indicia 15b and is reflected by the indicia at which the proximal end 2 of cannulated member 1 is substantially positioned. In the example shown in FIG. 7, the indicia appear in 5 mm increments and as shown in FIG. 6C, the total thickness T of the rotator cuff tendon 150 is 14 mm.

In an example, the method of measuring further comprises the step of calculating a percent of the tear in the tissue. The step of calculating is performed according to the following formula:

(depth of the tear of the tissue t/thickness of the tissue T)*100.

In the example shown schematically in the panels of FIG. 7, the percentage of the tear is:

(9 mm/14 mm)*100=64% of the tissue is torn.

Optionally, the percentage of the tissue that is torn, as determined by the relationship between the depth t of the tear and the thickness T of the tissue, is used to decide whether to surgically repair the tear in the tissue. In an example where the torn tissue is a rotator cuff tendon, the method further comprises the step of surgically repairing the tear when the percentage of the tear is greater than about 50%.

While the foregoing has been set forth in considerable detail, it is to be understood that the drawings, detailed embodiments, and examples are presented for elucidation and not limitation. Design variations, especially in matters of shape, size, and arrangements of parts, may be made but are within the principles of the invention. Those skilled in the art will realize that such changes or modifications of the invention or combinations of elements, variations, equivalents, or improvements therein are still within the scope of the invention as defined in the appended claims.

What is claimed is:

1. A measuring device for measuring a depth of a tear of a tissue and a total thickness of the tissue, the measuring device comprising:
    a member having a shaft and a distal tip, there being a plurality of indicia on the shaft of the member; and
    a cannulated member into which the member is slidably disposed;
    wherein the plurality of indicia comprises:
    a first plurality of indicia disposed on a distal portion of the shaft that is readable to measure the depth of the tear when the distal tip of the member is positioned at the distal margin of the tear and the measuring device is positioned substantially tangential to the tear; and
    a second plurality of indicia disposed on a proximal portion of the shaft that is readable to measure a total thickness of the tissue when the cannulated member is moved so that a distal end thereof is substantially at a proximal margin of the tissue while maintaining the position of the distal tip at the distal margin.

2. The measuring device as in claim 1 wherein the device is capable of being used to measure the depth arthroscopically.

3. The measuring device as in claim 1 wherein the distal tip is configured to penetrate through the tear.

4. The measuring device as in claim 1 wherein the cannulated member further comprises a window positioned on the cannulated member to view at least a portion of the second plurality of indicia.

5. The measuring device as in claim 1 further comprising a head disposed on the shaft at an end of the shaft opposite the distal tip.

6. The measuring device as in claim 1 wherein the cannulated member further comprises a grip.

7. The measuring device as in claim 1 further comprising a seal positioned on the shaft that stabilizes the shaft within the cannulated member.

8. The measuring device as in claim 1 wherein the tissue is a rotator cuff tendon.

9. The measuring device as in claim 1 wherein the device is made from at least one of stainless steel, titanium, PEEK, or a hard plastic.

10. A method of measuring a tear of a tissue and a total thickness of the tissue using a measuring device, the measuring device including a cannulated member having distal and proximal ends, a member slidably disposed within the cannulated member and having a distal tip and a shaft with distal and proximal portions, there being (i) a first plurality of indicia disposed on a distal portion of the shaft that is readable to measure the depth of the tear when the distal tip of the member is positioned at the distal margin of the tear and the measuring device is positioned substantially tangential to the tear, and (ii) a second plurality of indicia disposed on a proximal portion of the shaft that is readable to measure a total thickness of the tissue when the cannulated member is moved so that a distal end thereof is substantially at a proximal margin of the tissue while maintaining the position of the distal tip at the distal margin, the method of measuring comprising the steps of:

a. positioning the device substantially tangential to the tear;
b. sliding the member within the cannulated member so that the distal tip of the member is substantially positioned at the distal margin;
c. measuring the depth of the tear by reading a point on the first plurality of indicia that is equal to the distance between the distal margin and a distal edge of the tissue tear;
d. moving the cannulated member so that the distal end is substantially positioned at the proximal margin while substantially maintaining the position of the distal tip at the distal margin; and
e. measuring the thickness of the tissue by reading a point on the second plurality of indicia that is equal to a distance between the distal margin and a proximal edge of the tissue.

11. The method of measuring as in claim 10 further comprising the step of calculating a percent of the tear of the tissue, wherein the step of calculating is performed according to the following formula:

(the depth of the tear of the tissue/the thickness of the tissue)*100.

12. The method of measuring as in claim 10 wherein the steps are performed arthroscopically.

13. The method of measuring as in claim 11 further comprising the step of using the percent of the tear of the tissue to decide whether to surgically repair the tear.

* * * * *